United States Patent
Shin et al.

(10) Patent No.: US 7,282,384 B2
(45) Date of Patent: Oct. 16, 2007

(54) THERMOELECTRIC TRANSDUCING MATERIAL THIN FILM, SENSOR DEVICE, AND ITS MANUFACTURING METHOD

(75) Inventors: Woosuck Shin, Aichi (JP); Fabin Qiu, Aichi (JP); Noriya Izu, Aichi (JP); Ichiro Matsubara, Aichi (JP); Norimitsu Murayama, Aichi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 366 days.

(21) Appl. No.: 10/532,825

(22) PCT Filed: Nov. 11, 2003

(86) PCT No.: PCT/JP03/14318

§ 371 (c)(1),
(2), (4) Date: Apr. 26, 2005

(87) PCT Pub. No.: WO2004/044996

PCT Pub. Date: May 27, 2004

(65) Prior Publication Data

US 2006/0063291 A1    Mar. 23, 2006

(30) Foreign Application Priority Data

Nov. 12, 2002 (JP) ............................. 2002-327727

(51) Int. Cl.
*H01L 21/203* (2006.01)
*H01L 35/34* (2006.01)

(52) U.S. Cl. .................. 438/54; 438/488; 438/509; 257/467

(58) Field of Classification Search .................. 438/54
See application file for complete search history.

(56) References Cited

U.S. PATENT DOCUMENTS

| 7,166,796 B2 * | 1/2007 | Nicoloau | 136/201 |
| 2003/0056570 A1 * | 3/2003 | Shin et al. | 73/25.05 |
| 2004/0000333 A1 * | 1/2004 | Chen et al. | 136/224 |

FOREIGN PATENT DOCUMENTS

| JP | 53-95588 | 8/1978 |
| JP | 38650/1992 | 4/1991 |
| JP | 07-202274 | 8/1995 |
| JP | 11-003999 | 1/1999 |
| JP | 2000-292254 | 10/2000 |

OTHER PUBLICATIONS

Matsui, K. "Sensa Katsuyou 141 no Jiseki Nouhau (Specific applications of actual results and know-how of 141 uses of sensors)", Chapter 2, CQ Publishing, pp. 45-65 2001.

* cited by examiner

*Primary Examiner*—Stephen W. Smoot
(74) *Attorney, Agent, or Firm*—Oblon, Spivak, McClelland, Maier & Neustadt, P.C.

(57) ABSTRACT

The present invention provides an SiGe-based thin film, a method for manufacturing this thin film, and applications of this thin film. The present invention relates to a method for producing, by sputtering, an SiGe-based semiconductor thin film to serve as a member of a thermoelectric transducing material component that is a constituent element of a sensor device whose signal source is a temperature differential and that transduces a local temperature differential into an electric signal, wherein the SiGe-based thin film is produced by heat treating a SiGe-based semiconductor thin film material after sputtering vaporization; to the above-mentioned method for forming a thin film wherein the substrate temperature and/or the plasma output is raised in the formation of the SiGe-based semiconductor thin film by sputtering vaporization, to form a thin film with a more highly crystallized structure; to an SiGe-based thin film produced by the above-mentioned method, which serves as a member of a thermoelectric transducing material component that is a constituent element of a sensor device whose signal source is a temperature differential and that transduces a local temperature differential into an electric signal, and which has been endowed with good thermoelectric characteristics by heat treatment; and to a gas sensor device containing as a constituent element the above-mentioned SiGe-based thin film.

10 Claims, 11 Drawing Sheets

THERMOELECTRIC TRANSDUCING MATERIAL THIN FILM, SENSOR DEVICE, AND ITS MANUFACTURING METHOD

TECHNICAL FIELD

This invention relates to an SiGe-based semiconductor thin film to be applied in electronic devices such as thin film transistors used for high-speed operation at high frequency region, and to a method for manufacturing this thin film, and further to a semiconductor device using this semiconductor thin film. The SiGe-based thermoelectric transducing thin film material of the present invention is useful as a member for thermopiles, and more specifically, is used in sensors that detect as a voltage signal a change in a local temperature differential caused by heat generated in the catalytic reaction of a catalyst material, and is useful as a gas sensor or a similar device whose signal source is a local increase in temperature, such as an infrared sensor, for example.

BACKGROUND ART

In a device in which slight temperature changes or tiny amounts of thermal energy is detected, a sensor that works by transducing a temperature differential generated from a signal source into an electrical signal is used. In this kind of sensors, there is a thermopile type, which detects a temperature change as thermoelectromotive force by utilizing the Seebeck effect of a thermocouple or a thermopile, which consists of a plurality of these thermocouples connected in series. Other known types of device that detect temperature changes include a pyroelectric type, which detects a change in a floating charge produced by polarization corresponding to the thermal energy of infrared rays in a base material made of ceramic or the like (this type utilizes the pyroelectric effect), and a system which detects a change in resistance produced by the heat of a temperature-sensitive resistor formed from ultrafine wire or a thin film of metal or the like (this system utilizes resistance changes) [K. Matsui, *Sensa Katsuyou* 141 *no Jisseki Nouhau* (Specific applications of actual results and know-how of 141 uses of sensors), chapter 2, CQ Publishing, 2001].

Of these, thermoelectric transducing devices that utilize the Seebeck effect are commonly used in infrared sensors, for example, because they are best for measuring temperature or for monitoring temperature differentials. The thermoelectric transducing material thin film (hereinafter referred to as thermoelectric thin film) used for these thermoelectric transducing devices is usually what is known as a metal-based thermoelectric semiconductor, which exhibits high electroconductivity and has a high Seebeck coefficient, such as bismuth (Bi), tellurium (Te), or antimony (Sb) (see, for example, Japanese Laid-Open Patent Publication No. 2000-292254).

These materials, however, are highly toxic, and furthermore there are many limitations on their film formation and working processes. In the case of the above-mentioned metal-based thermoelectric thin film materials, it is difficult to etch the film after being formed into a thin film, and it is no easy task to form a pattern by a process such as lift-off. Actually, the most common approach with these materials is to form a thin film directly by vapor deposition through a metal mask. With this process, though, it is difficult to perform finer working, and limits of width of a line to be processed make it difficult to raise the degree of integration thereof.

Similarly, SiGe is an example of a material that exhibits high thermoelectric transducing efficiency while also being easy to process and having low toxicity. SiGe-based thermoelectric materials have a long history of application, including use as a thermoelectric material in the space development, and in more recent years semiconductor thin films based on SiGe alloys have been widely used as members for devices to be used at high-temperature operations and for devices used in high-speed communications.

Known methods for manufacturing an SiGe thin film include a method in which hydrogen or $GeF_3$ is mixed into silane ($SiH_4$) gas, and a thin film is deposited by vacuum CVD or plasma CVD while being crystallized, and a method in which an amorphous thin film is formed on a substrate as an amorphous precursor, and this thin film is then crystallized. The former method, in which a deposited thin film is crystallized, promotes crystallization simultaneously with the formation of the thin film, but its drawbacks include the high cost of the processing equipment and the need to subject the substrate itself to a relatively high temperature of 600° C. or higher. Solid-phase growth method in which annealing is performed over an extended period is known as a type of the latter method in which an amorphous silicon thin film is first formed and then crystallized, but this method is impractical because it takes so long, and another drawback is higher manufacturing cost.

Also, when CVD is employed for forming a crystalline or amorphous semiconductor thin film, since the film contains about 2 to 20 at % hydrogen, an annealing treatment in an electric furnace is necessary to remove the hydrogen gas from the film. This process requires that annealing for degasification be performed at high temperature for an extended period, and this hampers efforts at increasing productivity, and the heat involved in the degasification treatment causes the substrate to deform, or contaminants from the substrate are diffused in the thin film, among other such problems.

One heat treatment method involves crystallizing the material by irradiating it with an excimer laser. An amorphous thin film or a polycrystalline thin film is formed on a substrate and irradiated with an excimer laser to heat and crystallize the thin film. With this technique, however, it is extremely difficult to maintain a consistent crystal quality in the thin film, and variance tends to occur in the electrical characteristics of the manufactured thin film as well.

DISCLOSURE OF THE INVENTION

In light of the above situation, the present invention was developed in order to solve the above problems encountered with prior art, and it is an object of the present invention to provide a method for producing an SiGe-based semiconductor thin film to serve as a member of a thermoelectric transducing material component that is a constituent element of a sensor device whose signal source is a temperature differential and that transduces a local temperature differential into an electric signal, an SiGe-based thin film which has been endowed with good thermoelectric characteristics by this method, and a sensor device.

A further object of the present invention is to provide means for overcoming the limitations to the operating temperature resulted in a conventional device due to varieties of the gas selectivity of a catalyst generated with the operating temperature.

To solve the above problems, the present invention is constituted by the following technological means.

(1) A method for producing an SiGe-based semiconductor thin film to be served as a member of a thermoelectric transducing material component that is a constituent element of a sensor device whose signal source is a temperature differential and that transduces a local temperature differential produced by a selective catalyst reaction into an electric signal, comprising the steps of:

1) forming an SiGe-based semiconductor thin film over a substrate by sputtering vaporization; and 2) heat treating the SiGe-based semiconductor thin film material after the sputtering vaporization.

(2) The method according to (1) above, wherein the heat treatment is performed at a temperature of from 600° C. to 1000° C.

(3) The method according to (1) above, wherein the substrate temperature and/or the plasma output is raised in the formation of a SiGe-based semiconductor thin film by sputtering vaporization method, to form a thin film with a more highly crystallized structure.

(4) The method according to (1) above, wherein the heat treatment is performed by furnace annealing with a controlled atmosphere using an ordinary electric furnace, or by rapid thermal process using an infrared lamp heating apparatus capable of atmosphere control.

(5) The method according to (1) above, wherein, during sputtering, a thin film is produced by first doping an SiGe target with an impurity, and during heat treatment, the gas atmosphere, temperature, heat treatment duration, and temperature elevation time are controlled, so that crystallization is performed while the amount of impurity in the semiconductor thin film is controlled.

(6) The method according to (1) above, wherein, during heat treatment, the heat treatment conditions are controlled, an insulator thin film of an oxide is grown over the semiconductor thin film, and crystallization is performed while an insulation layer is produced.

(7) The method according to (1) above, wherein, during the sputtering vaporization of the SiGe-based thin film, the temperature of the heat treatment can be lowered by vapor depositing a transition metal typified by nickel.

(8) The method according to (1) above, wherein a sensor device whose signal source transduces a local temperature differential produced by a selective catalyst reaction into an electric signal is exposed to a volatile organosilicon gas to form a thin film on the surface thereof, thereby increasing the gas selectivity thereof.

(9) An SiGe-based thin film produced by the method according to any of (1) to (8) above, which serves as a member of a thermoelectric transducing material component that is a constituent element of a sensor device whose signal source is a temperature differential and that transduces a local temperature differential into an electric signal, and which has been endowed with good thermoelectric characteristics by heat treatment.

(10) A gas sensor device containing as a constituent element the SiGe-based thin film according to (9) above.

The present invention will now be described in further detail.

In the present invention, a SiGe-based semiconductor thin film is used as a member of a thermoelectric transducing material component that is a constituent element of a sensor device whose signal source is a temperature differential and that transduces a local temperature differential into an electric signal, and thereby a high-performance sensor device can be realized. With the present invention, a higher output signal and lower noise are obtained, for example, when an oxide thermoelectric material is used as the thermoelectric transducing member of this type of gas sensor device (W. Shin et al., "Thermoelectric thick-film hydrogen gas sensor working at room temperature," *Jpn. J. Appl. Phys.*, 40, 11B, pp. L1232-L1234, 2001). This is because the thermoelectric transducing performance of the SiGe-based material is superior to that of an oxide.

Also, with the present invention, sputtering method is used to produce a SiGe-based semiconductor thin film. This is preferable in the production of a device with high performance and stable characteristics, and furthermore makes it possible to produce a satisfactory semiconductor thin film in a short time and with a simple manufacturing process. Furthermore, simultaneous patterning with a metal mask is possible, allowing the overall process to be simplified.

However, problems encountered with an SiGe thin film produced by sputtering method were that its resistance was high, the signal output had poor stability, and so forth. Research conducted by the inventors has revealed that this is the reason for the poor crystallinity of the vapor deposited thin film. In view of this, in the present invention, a thin film material that has relatively poor crystallinity after sputtering vaporization is subjected to a heat treatment, which improves crystallinity and allows the required characteristics to be imparted.

Further, with the present invention, the heat treatment can be simplified by making a thin film with increased crystallinity, even if only slightly, in the vaporization of the thin film, and this allows a completely novel semiconductor thin film to be manufactured. Accordingly, with the present invention, the substrate temperature and/or the plasma output is raised in the process of the crystallization of an amorphous thin film, thereby a thin film with a more highly crystallized structure is formed, even in the state immediately following vaporization.

In the present invention, these heat treatments can be accomplished, for example, by furnace annealing, using an ordinary electric furnace and a controlled atmosphere. Also, a crystalline thin film that is easier to control can be manufactured by employing a rapid thermal process in which an infrared lamp heating apparatus is used to raise the temperature elevation rate during the heat treatment. However, the method and means for the heat treatment are not limited to these with the present invention.

Furthermore, crystallization can be performed while the amount of impurity in the thin film is controlled, and a crystalline thin film can be manufactured, by controlling the gas atmosphere, temperature, heat treatment duration, and temperature elevation time during the heat treatment. Also, with the present invention, sputtering vaporization can be performed with a single target if the target is an SiGe alloy semiconductor to start with, or, the target can be first doped with an impurity element prior to sputtering vaporization, and impurity element doping can be performed simultaneously with the formation of the film during thin film vaporization, allowing a doped semiconductor thin film to be produced.

In the heat treatment, an oxide is produced on the surface of the thin film by the oxygen partial pressure in the atmosphere. This oxide is a silicon oxide composed of silicon and oxygen, and grows while consuming the silicon that is a component of the SiGe thin film. The SiGe can even disappear if the oxide film is grown in large enough quantity. In the process, the germanium component is purged from the silicon oxide film and collects at the interface with the SiGe (Nayak, D K et al., Kinetics and mechanism of oxidation of SiGe: dry versus wet, *Appl Phys. Lett.* 73, p. 644, 1989).

The process for forming insulated thin film that is required for the wiring and so forth of devices can be omitted with the present invention by utilizing this oxide. With the present invention, it is possible to form an insulated thin film of an oxide grown on the SiGe semiconductor thin film, and to produce this insulated layer crystallized for manufacturing a crystalline thin film by controlling the process is conditions including the atmosphere of the heat treatment. An advantage of the present invention is that the step of forming the insulated film can be omitted by forming an insulated film of an oxide on the surface of the semiconductor thin film as a semiconductor thin film formed on an insulating substrate.

In the present invention, an SiGe-based semiconductor thin film is produced by sputtering to be served as a member of a thermoelectric transducing material component that is a constituent element of a sensor device whose signal source is a temperature differential and that transduces a local temperature differential produced by a selective catalyst reaction into an electric signal. Thus, with the present invention, an SiGe-based semiconductor thin film is formed by sputtering method in order to produce a satisfactory semiconductor thin film in a short time, but since the thin film will have relatively poor crystallinity with vaporization alone in this case, the thin film material is heat treated after the vaporization to increase its crystallinity and endow it with the required characteristics.

This heat treatment is preferably performed by so-called furnace annealing using an ordinary electric furnace with a controlled atmosphere. This heat treatment is performed in an argon atmosphere, for approximately 5 to 24 hours at a treatment temperature of 700 to 1000° C. Problems such as almost no crystallization occurring will be encountered if the treatment temperature is under 700° C., but it is also undesirable for the temperature to be over 1000° C. because this high-temperature process will accompany with reactions with the substrate and other problems. The heat treatment temperature can be lowered by raising either the substrate temperature or the plasma output during sputtering vaporization. The effect of this is most clearly apparent when the substrate temperature is at least 100° C. In the case of plasma output, the effect will be pronounced from 200 W and up with a 3-inch target. This method forms a thin film with a more highly crystallized structure, even in the state immediately following the vaporization, and this method also has the effect of lowering the heat treatment by about 100° C. Therefore, the heat treatment can be performed at 600° C. or higher in this case.

Further, with the present invention, the heat treatment duration can be reduced to no more than 30 minutes by using a rapid thermal process featuring an infrared lamp heating apparatus capable of controlling the atmosphere. In the heat treatment, crystallization can be performed while controlling the gas atmosphere, temperature, the heat treatment duration, and the temperature elevation rate, and further controlling the amount of impurity in the SiGe thin film. Also, an oxide produced over the SiGe semiconductor thin film after heat treatment can be utilized as an insulation layer. For example, the heat treatment is performed such that the thickness of the insulation layer produced on the surface of an SiGe semiconductor thin film of approximately 600 nanometers will be approximately 100 nanometers. Since this film can be utilized as an insulation layer, a window is subsequently made in just the portion where electrical contact is necessary. With the present invention, the SiGe thin film produced by the above method can be utilized along with a suitably catalyst material to create a suitable gas sensor device. In this case, a platinum catalyst for hydrogen detection was used as the catalyst material in the examples given below, but the present invention is not limited to this, and any suitable catalyst material can be used.

The amount of doping of the thin film, and whether the film is n type or p type, can be controlled by controlling the gas atmosphere, temperature, heat treatment duration, and temperature elevation time during the heat treatment. This is because an SiGe alloy semiconductor naturally tends to be n type, and sputtering vaporization can be performed by doping the target ahead of time with an n type impurity element.

It is also possible to form a thin film on a substrate that is not stable at high temperature, such as glass or plastic, by lowering the temperature of the heat treatment required for crystallization. The addition of a transition metal, as recently reported, is an effective way to further lower the crystallization temperature of an SiGe material (C. Hayzelden and J. Batstone, *J. Appl. Phys.,* 73 (1993), 8279-8289).

With a gas sensor that utilizes a reaction at the catalyst surface, its performance is decreased by the production of a film of impurities or the like on the catalyst surface. A typical example of this is the poisoning of a catalyst by a volatile organosilicon (such as hexamethyldisilane, HMDS) gas. This volatile organosilicon lowers catalytic activity by forming a film of silicon oxide on the catalyst surface. Nevertheless, a structure with which selective gas permeation is possible will be formed under certain film production conditions, and a selective catalyst reaction can be induced. Such a film is sometimes intentionally formed on a ceramic sensor surface. One known method for increasing the gas selectivity of a gas sensor is to form what is known as a molecular sieve, which is a physical filter, on the surface of the sensor material of a gas sensor by chemical vapor deposition method (CVD). (See, for example, A. Katsuki and K. Fukui, $H_2$_selective gas sensor based on $SnO_2$, Sensors and Actuators B, 52, pp. 30-37 (1998)).

The effects of the present invention are (1) a sensor device whose signal source transduces a local temperature differential produced by a catalyst reaction into an electric signal is exposed to a volatile organosilicon gas to form a thin film on the surface thereof, thereby increasing the gas selectivity thereof, (2) the device temperature must be raised high in order to form a film on a catalyst surface by chemical vapor deposition method, and performing this process adversely affects the properties of the catalyst, but with the present invention, a thin film is formed on the surface of the device by exposing the device to a volatile organosilicon gas at a relatively low temperature below 200° C., which is near the operating temperature of the device, and this product is then heat treated at a higher temperature, which forms a solid film while preventing catalyst degradation, and this increases gas selectivity, (3) the gas selectivity of the device can be increased by forming a thin film on the surface of the device by exposing it to a volatile organosilicon gas, and (4) the gas selectivity can be increased by forming a thin film on the surface of the device by exposing it to a volatile organosilicon (hexamethyldisilane, HMDS) gas.

BEST MODE FOR CARRYING OUT THE INVENTION

Figure 1:
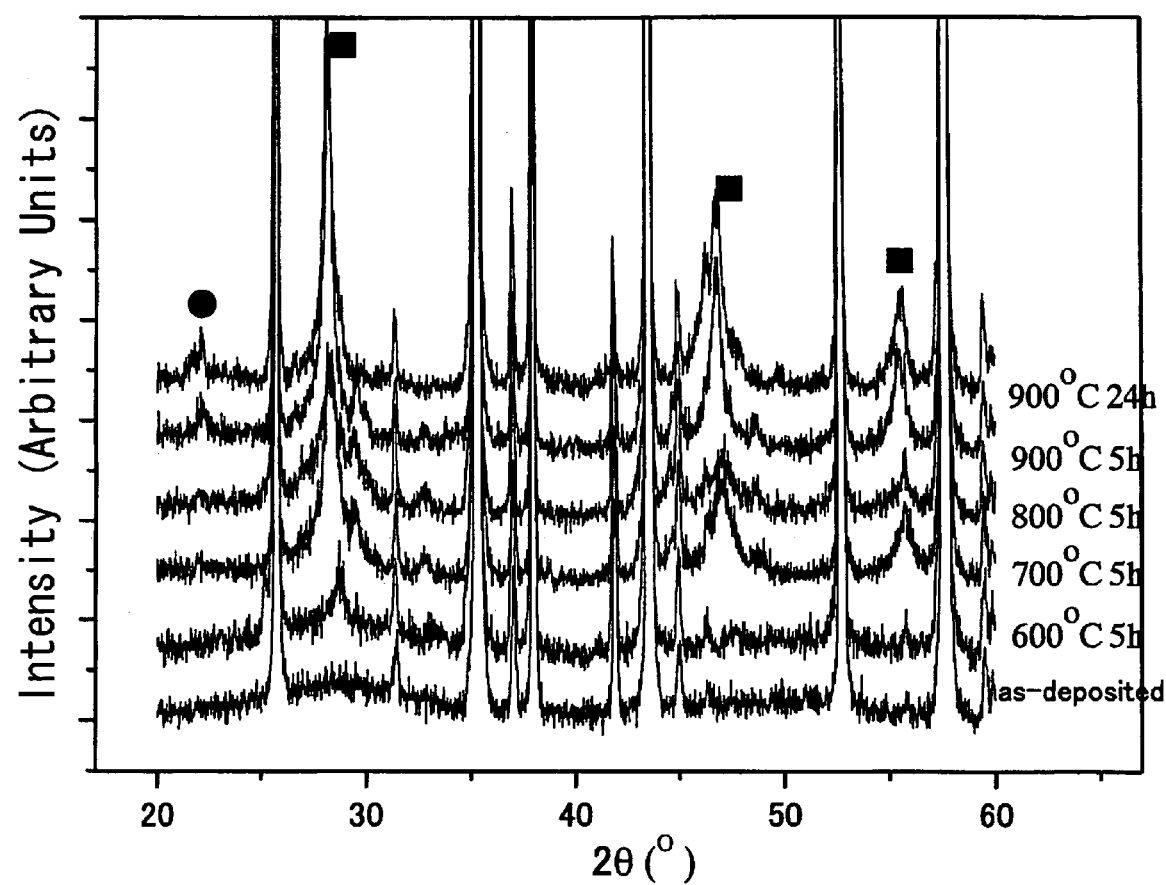
FIG. 1 shows the X-ray diffraction patterns of SiGe thin films produced by sputtering vaporization.

The present invention will now be described in more specific terms through examples, but the present invention is not limited in any way by the following examples.

EXAMPLE 1

(1) Production of Gas Sensor

In this example, a gas sensor capable of measuring gas concentration over a wide range and at high selectivity was produced by utilizing a catalyst exhibiting a selective catalytic oxidation reaction for a specific type of flammable gas. The production procedure in one example of a gas sensor device to which the process of the present invention is applied consists of production of a thermoelectric thin film by sputtering, heat treatment, and formation of a platinum catalyst film, in that order.

1) Target Production

1% phosphorus was mixed into an SiGe alloy (80% Si, 20% Ge), this mixture was pulverized to an average particle size of just a few microns or less in a planetary ball mill, and the resulting powder was molded and then sintered (by hot pressing) for 5 hours at 1000° C. to produce a sinter. This sinter was used as a sputtering target.

2) Thermoelectric Film Production

Using the above target, a film of an SiGe thermoelectric transducing material was formed with a high frequency (RF) sputtering apparatus. This sputtering was performed at a vapor deposition pressure of approximately $5 \times 10^{-1}$ Pa and a sputtering output of 250 W. Sputtering vaporization was conducted under these conditions for 30 minutes, forming a film of approximately 0.7 micrometer. The thickness of this film was determined from direct observation of a fracture plane thereof using an electron microscope.

3) Heat Treatment

An SiGe thin film with increased crystallinity was produced by placing the SiGe thin film that had undergone sputtering vaporization in a furnace with an argon atmosphere and heat treating it for approximately 5 hours at 900° C. In this heat treatment, the temperature, duration, and oxygen partial pressure in the atmosphere were controlled, and a thin oxide was produced on the surface of the thin film under an argon flow. This oxide was silicon oxide composed of silicon and oxygen, part of which was removed with an HF-based etching solution, forming an area of electrode contact (called a window). The window pattern was formed by photolithography.

4) Sputtering Vaporization of Catalyst Thin Film

A catalyst thin film was formed by sputtering vaporization over part of the device surface that had undergone the above process. To form this film in a pattern, the sputtering vaporization was performed with a metal mask placed over the device. The catalyst material here was a platinum catalyst in order to detect hydrogen. The catalyst film was produced by sputtering vaporization using a platinum target and a high frequency (RF) sputtering apparatus, at a sputtering output of 100 W for 10 minutes and at a vapor deposition pressure of approximately $2 \times 10^{-1}$ Pa.

5) Electrode Formation

A gold lead wire pattern was formed by sputtering vaporization using a metal mask, thereby forming wiring for signal take-off. The pattern was produced by sputtering vaporization using a gold target and a high frequency (RF) sputtering apparatus, at a sputtering output of 100 W for 5 minutes and at a vapor deposition pressure of approximately $2 \times 10^{-1}$ Pa.

6) Performance Evaluation

The performance of the catalyst and the device was evaluated by using an infrared thermal camera to find the surface temperature of the thin film catalyst formed on the substrate. The gas used in the test was allowed to flow into the test reaction chamber at a flux of approximately 100 cc/minute. Just as with the gas sensor device, changes in the surface temperature were measured with the infrared thermal camera under a mixed gas flow, and the output signal from the device was measured at the same time. The thermoelectric characteristics of the SiGe semiconductor thin film were evaluated in the air between room temperature and approximately 400° C. A steady-state method with high Seebeck coefficient reliability was used as the evaluation method.

(2) Results

The effects of the present invention will now be described on the basis of the results of evaluating the characteristics of the sensor device produced in the above process and its performance as a sensor.

1) Effect of Heat Treatment

An SiGe thin film that was not heat treated had poor characteristics, such as variance in its performance when the operating temperature was raised. Specifically, a thermoelectric gas detection sensor was produced by forming a layer of platinum catalyst in a thickness of about 50 nanometers with a sputtering apparatus over half of the SiGe thin film surface following sputtering vaporization, but the sensor device produced from this thin film had high resistance and its signal output was inconsistent, which meant that reproducibility was poor.

The reason for this lies in the low crystallinity of a thin film produced by sputtering. Analysis of the X-ray diffraction pattern confirmed that the vapor deposited thin film was not crystalline, but amorphous. FIG. 1 shows this XRD pattern. An attempt to measure the resistance of the thin film was also made by four-terminal method, but the resistance of the vapor deposited thin film was so high that measurement was impossible.

Meanwhile, an SiGe thin film produced by sputtering vaporization was placed in a furnace with an argon atmosphere and heat treated for about 5 hours near 900° C., which increased the crystallinity. As shown in FIG. 1, this can be clearly confirmed from analysis of the X-ray diffraction pattern after heat treatment. The vapor deposited thin film was confirmed to be not crystalline, but amorphous. In the figure, the peaks marked with a square were produced by SiGe crystals. Those peaks with no mark were produced by the substrate. When the crystallinity was checked while gradually raising the heat treatment temperature from 600° C., strong peaks attributable to SiGe were measured, particularly from heat treatment at 700° C. and up. Specifically, this indicates that crystalline SiGe began to grow in the thin film, which was amorphous. Crystallization was substantially completed by heat treatment at 900° C. It was found that there was not much change in the degree of crystallization when heat treatment was continued for a long time at this temperature. Conversely, if the heat treatment was continued too long, it was found that the process of oxidation began even at the low oxygen partial pressure present in the argon atmosphere, and the production of silica and $SiO_2$ began. The peaks near 22 degrees marked with a circle in the figure were produced by silica.

2) Evaluation of Sensor Device

Figure 2:
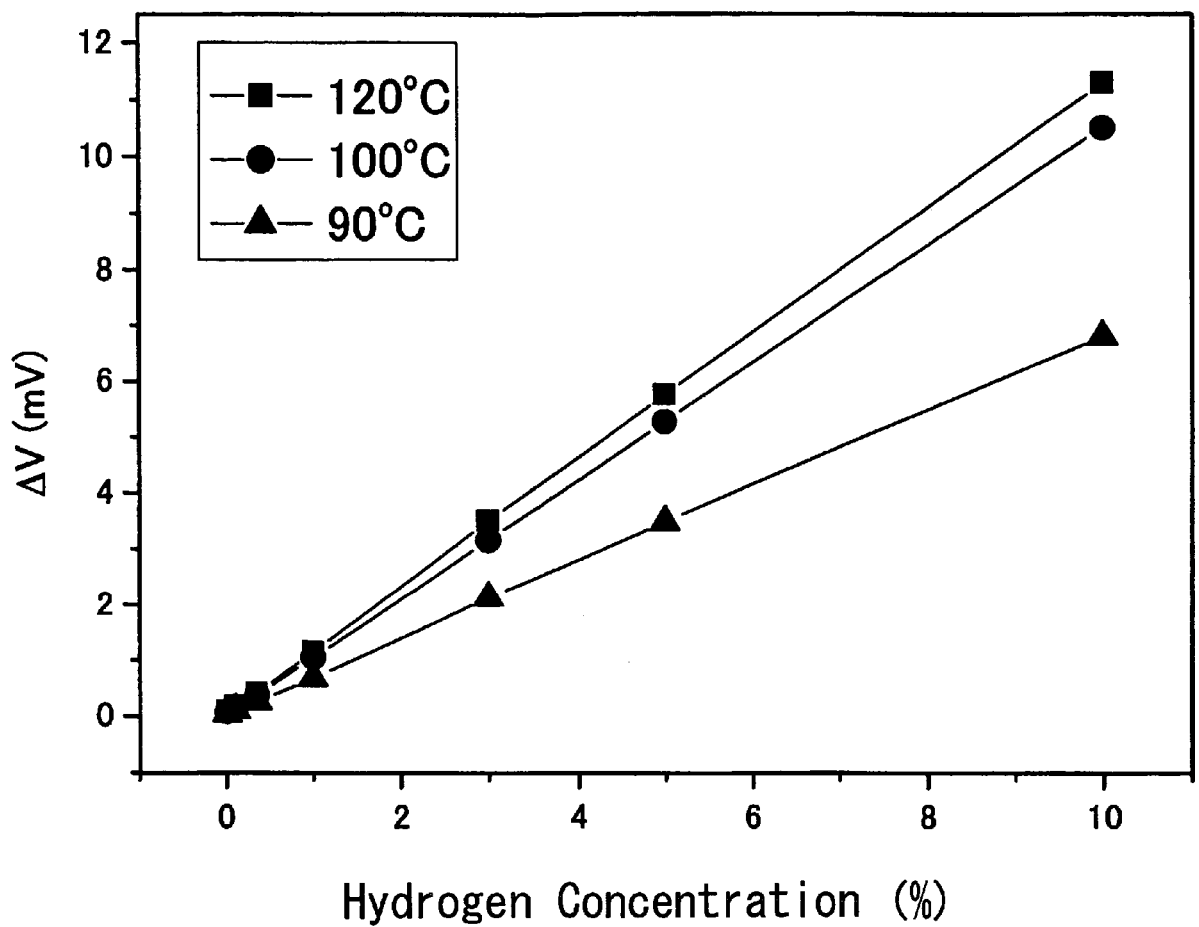
FIG. 2 is a graph of the hydrogen concentration and output characteristics of an SiGe thin film in a thermoelectric hydrogen gas sensor at the operating temperature.

A sensor was produced by vapor depositing platinum (serving as the catalyst) in a thickness of several dozen nanometers over half of a thick film surface, and this catalyst film was formed with a sputtering apparatus, just as with SiGe. The sputtering was performed at a vapor deposition pressure of approximately $4 \times 10^{-2}$ Torr and a sputtering output of 100 W for 5 minutes. FIG. 2 shows the hydrogen detection characteristics of this sensor. It can be seen that very linear output characteristics were obtained versus hydrogen concentration. The voltage output rises with operating temperature, but levels off at high temperature. These characteristics are dependent on the characteristics of the platinum catalyst.

Figure 3:
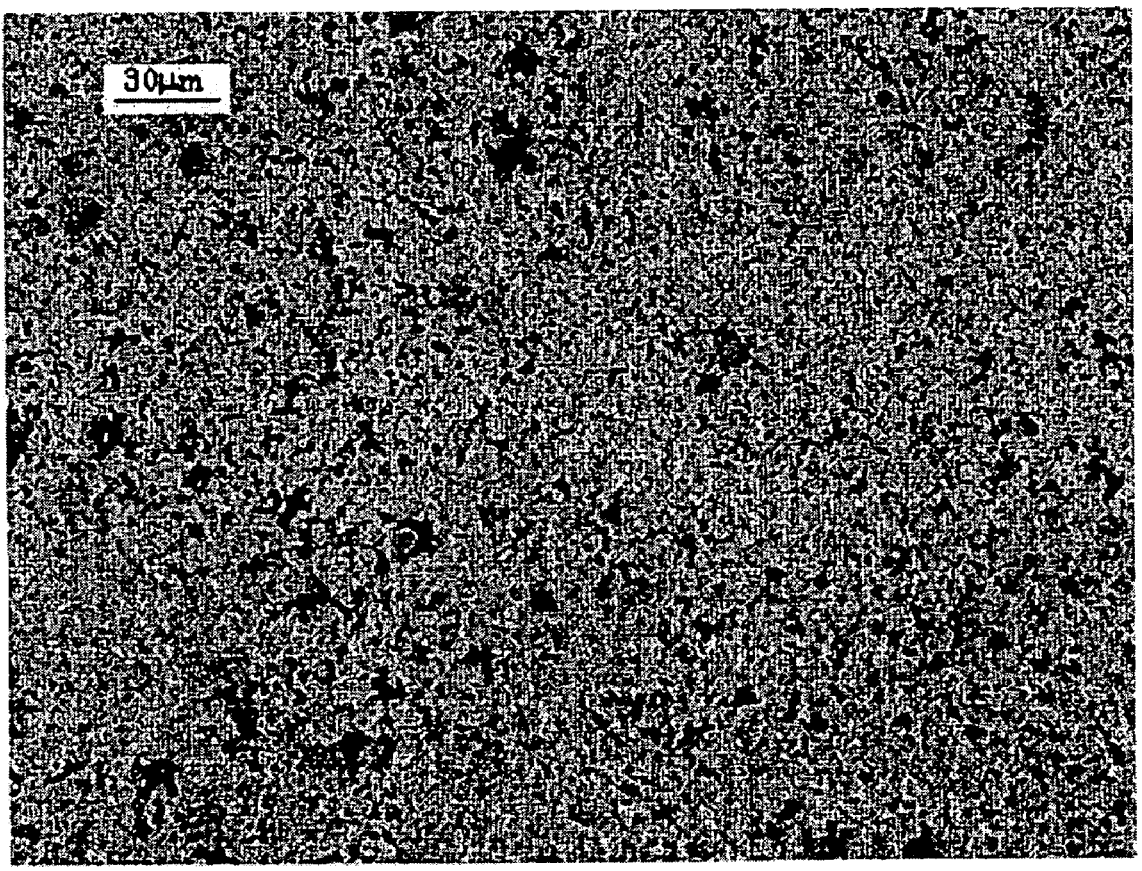
FIG. 3 shows the surface of a sensor device observed under an electron microscope.
Figure 4:
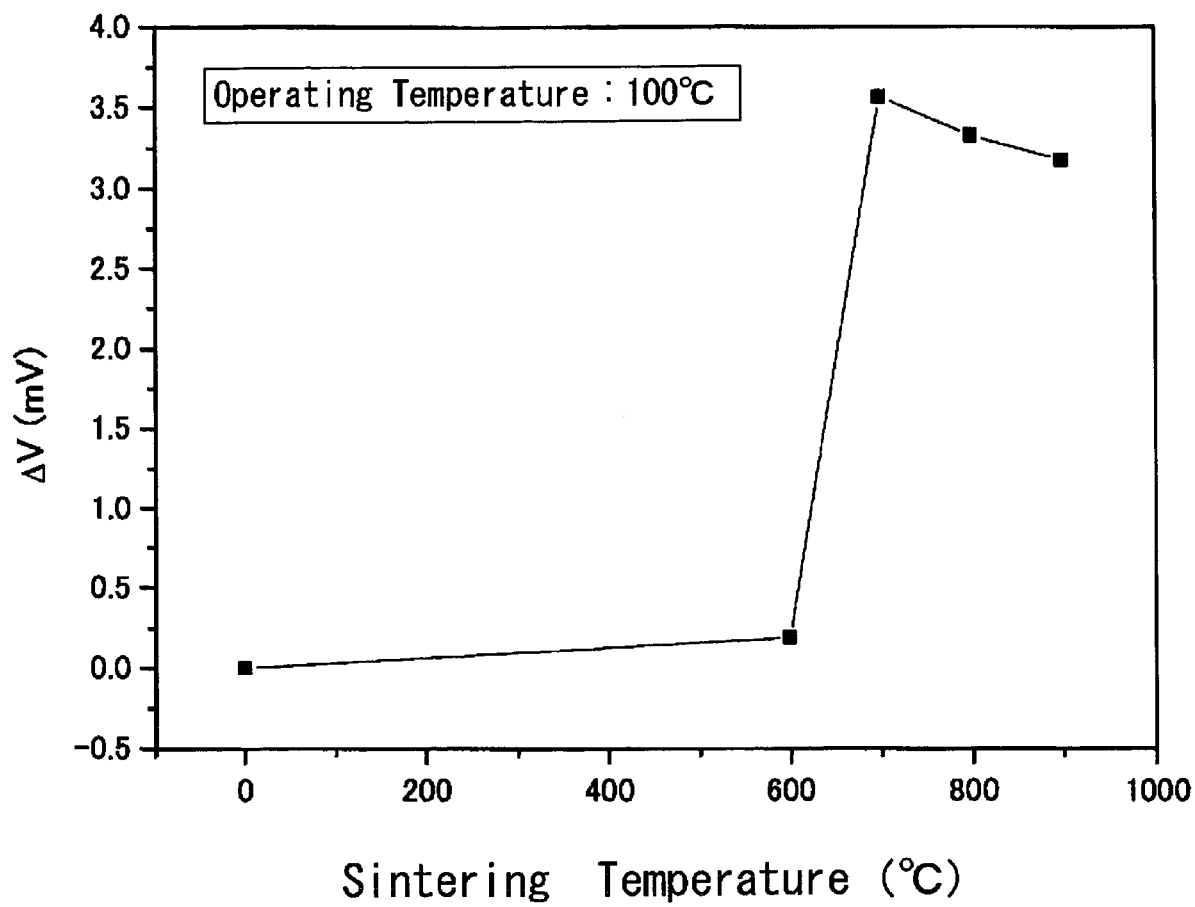
FIG. 4 is a graph of the improvement in voltage signal and device characteristics as a function of heat treatment temperature.

FIG. 3 shows an electron micrograph of the surface of a sensor device consisting of SiGe and platinum catalyst. It can be seen that the SiGe thin film has a particle structure and forms a solid film. The degree of crystallinity of this film, that is, how much the film is crystallized, affects the ultimate device characteristics. FIG. 4 shows the relationship between heat treatment temperature and voltage signal. It can be seen that crystallization increases with the heat treatment temperature, and as a result, the device characteristics tend to be improved. A comparison of the crystallization results in FIG. 1 reveals that crystallization increases and a stable sensor signal output is obtained when the heat treatment temperature is raised.

Figure 5:
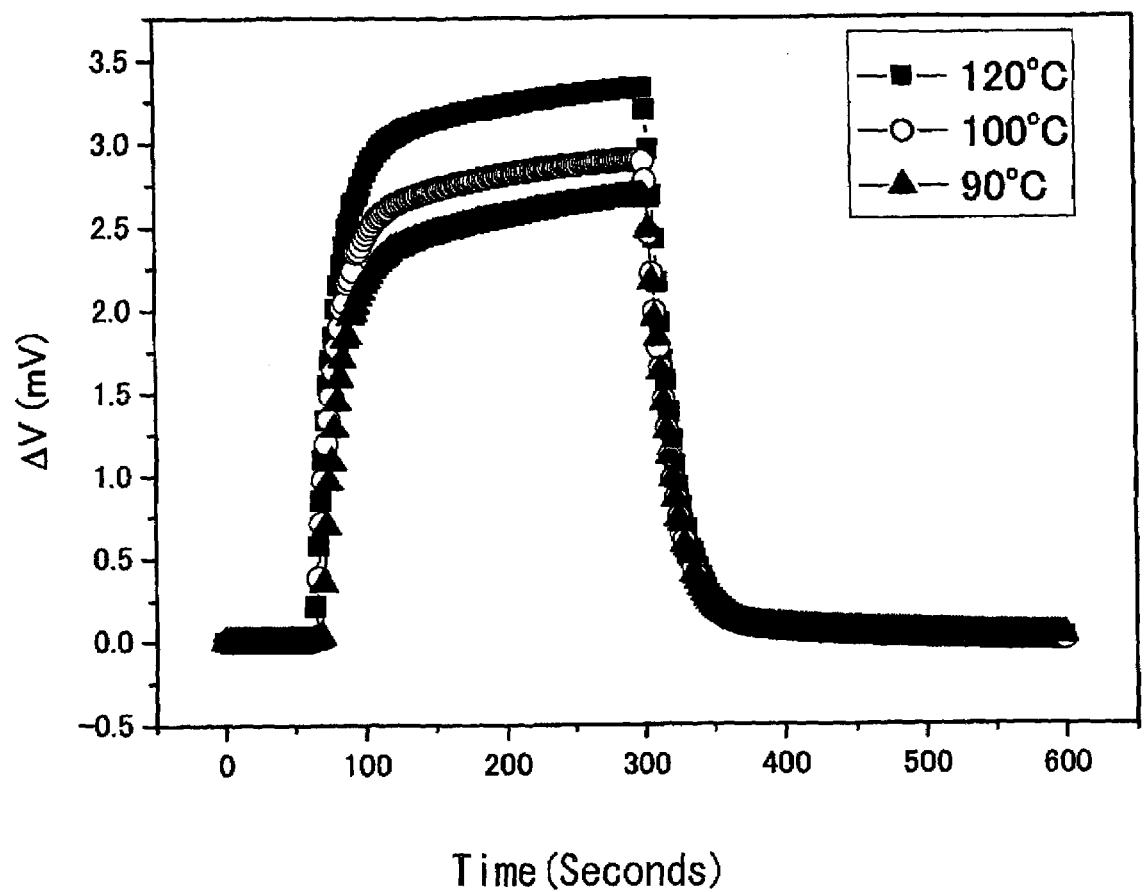
FIG. 5 is a graph of the response characteristics of a produced sensor device.
Figure 6:
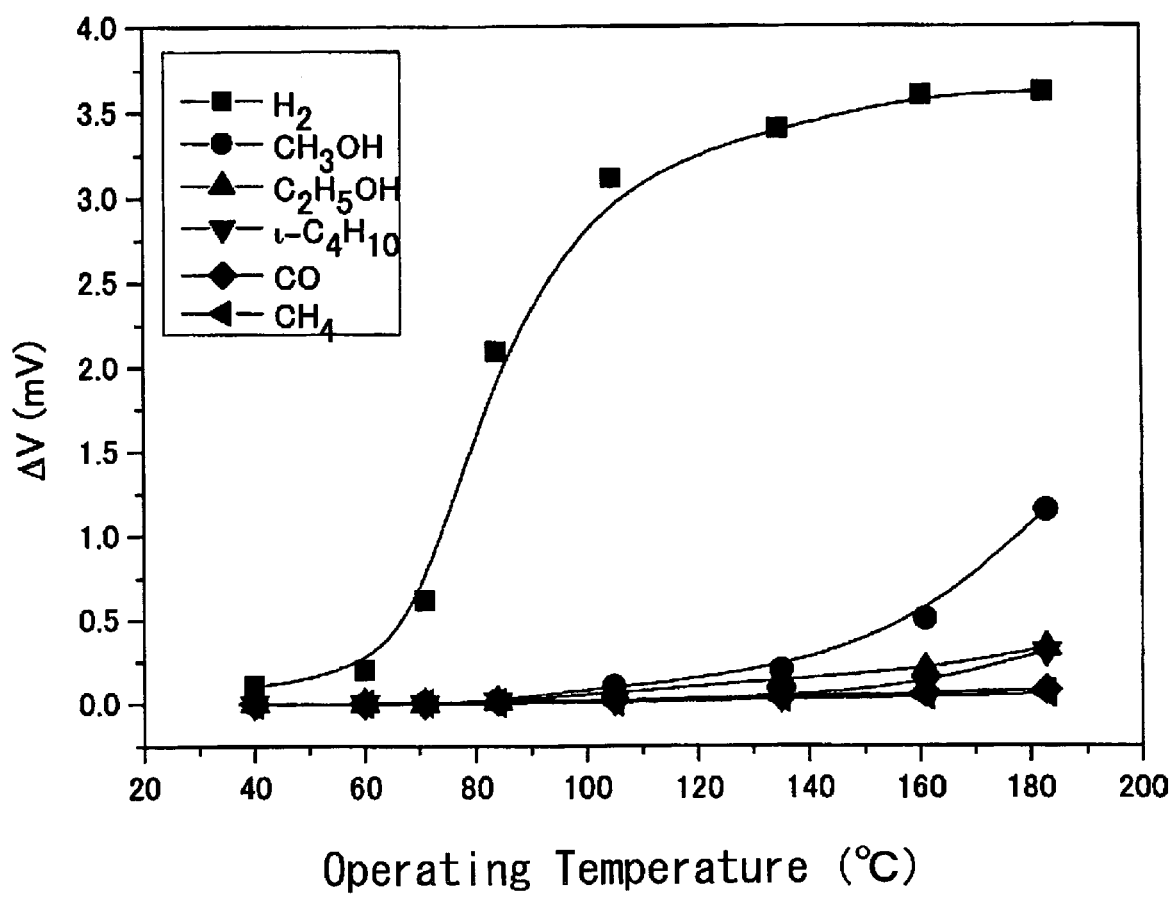
FIG. 6 is a graph of the results of an experiment comparing the selectivity of a produced hydrogen gas sensor for hydrogen and other flammable gases.

FIG. 5 shows the response characteristics of the sensor device. FIG. 6 shows the results of an experiment in which the hydrogen selectivity as a hydrogen sensor was compared to that for other flammable gases. In principle, higher selectivity should indeed be obtained when platinum is used as the catalyst, and as shown in the graphs, at about 150° C. or lower there was almost no response to gases other than hydrogen. This proves that a thermoelectric hydrogen sensor made from SiGe functions adequately as a hydrogen sensor.

3) Simultaneous Production of Oxide Film by Heat Treatment

Even though the heat treatment was performed while argon gas was allowed to flow into an electric furnace at about 100 ccm, a small amount of oxygen partial pressure was still present in the furnace. This oxygen reacted with the SiGe at high temperature, forming silica, a thin film of silicon oxide on the surface of the SiGe thin film. Because this is an insulator through which electricity cannot flow, this silica must be removed when an SiGe thin film is used. With the present invention, however, only the part of this insulation layer that is required for electrical contact is removed, rather than the entire layer, and a window measuring 60 microns square was provided for this purpose.

The etching for this window was performed for approximately 60 seconds using a 1:6:4 solution of $HF:H_2O:NH_4F$, which is what is ordinarily used for etching silica. As a result, the etching solution removed just the window portion of the silica. After this, an electrode pattern was formed and electrical resistance was measured, which confirmed that a good electrical connection had been formed on the SiGe surface. This tells us that an oxide film produced simultaneously during the crystallization process can be effectively utilized as an insulation layer.

4) Change in Crystallization Due to Sputtering Conditions

A problem with using a high temperature during heat treatment is that it can make other processes difficult. In an effort to lower this temperature or make heat treatment unnecessary, an attempt was made to create a thin film with somewhat higher crystallinity during sputtering vapor deposition. Three variables of the process conditions, namely, distance between the substrate and the target, argon gas flux, and vapor deposition time, did not greatly affect crystallization. However, the crystallization of the thin film changed markedly when the plasma output in sputtering was raised over 200 W. When an SiGe thin film was vapor deposited for 30 minutes at 250 W, an SiGe peak was confirmed from the X-ray diffraction pattern even without any heat treatment. When heat treatment was performed after this, crystallization proceeded even further, and peak intensity rose. The SiGe thin film vapor deposited at a high output of about 250 W had much higher crystallinity even at a low heat treatment temperature of 700° C., the result being the effect of lowering the heat treatment temperature by about 100° C. or more. It was also found that a similar effect is obtained either by raising the substrate temperature of raising the sputtering plasma output.

5) Process by which Doping Amount can be Controlled (Part 1)

Figure 7:
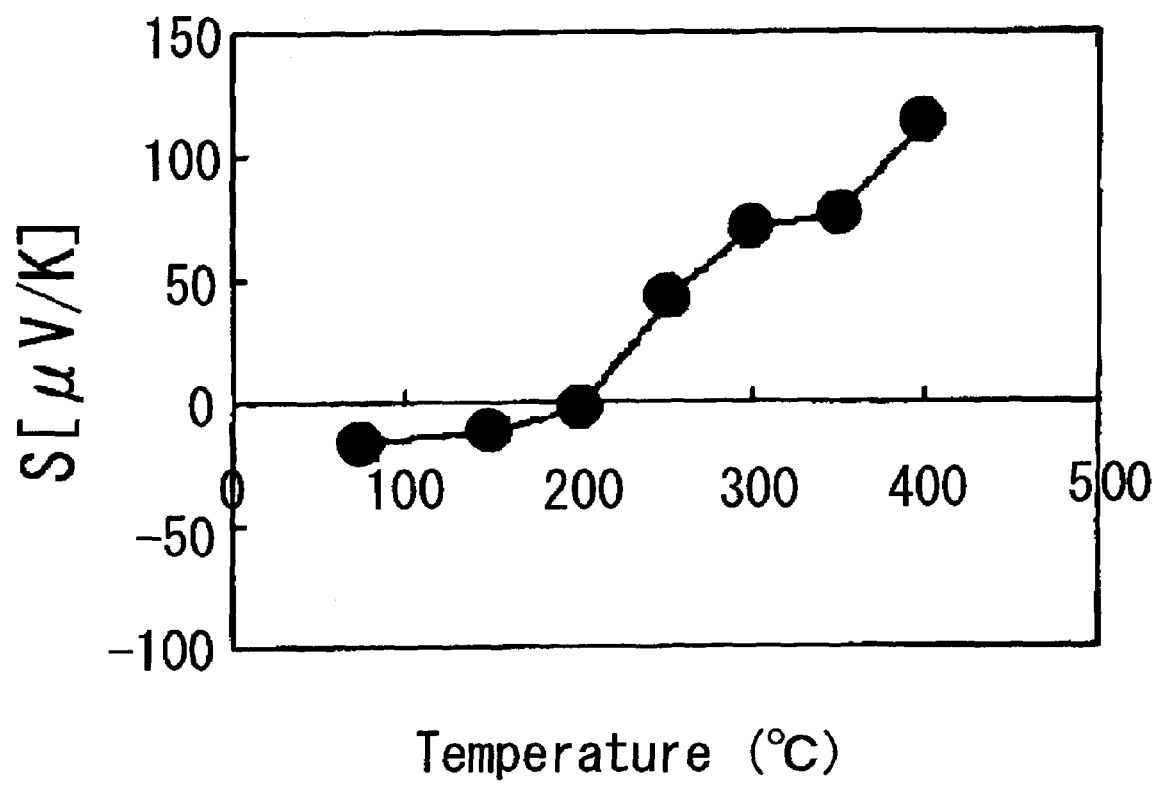
FIG. 7 is a graph of the temperature dependence of the Seebeck coefficient of an SiGe thin film.

When an SiGe target is pre-doped with an impurity, a problem is that the doped component, such as impurity phosphorus, is evaporated by the heat treatment, which markedly reduces the doping amount, but if the heat treatment temperature can be lowered, or if the device can be used directly without any heat treatment at all, then the doped component can be left intact. FIG. 7 shows the temperature dependence of the Seebeck coefficient of the sample in an example of this. The sample was produced by vapor deposition for 40 minutes at a sputtering output of 250 W and a substrate temperature of 300° C., using a phosphorus-doped SiGe target.

The thin film was then subjected to heat treatment for 5 hours at 900° C. while argon was allowed to flow through an ordinary electric furnace. As shown in FIG. 7, at a low temperature, the effect of doping was that this product exhibited n type characteristics, the Seebeck coefficient was negative, and the main charge carrier of the sample was electrons.

Meanwhile, when the evaporation of phosphorus was aided by extending the heat treatment duration, the amount of residual phosphorus decreased, and the sample became p type. A characteristic of this sample was that when the temperature was raised, the charge carrier became holes, and the sign of the Seebeck coefficient inverted to positive.

6) Process by which Doping Amount can be Controlled (Part 2)

Figure 8:
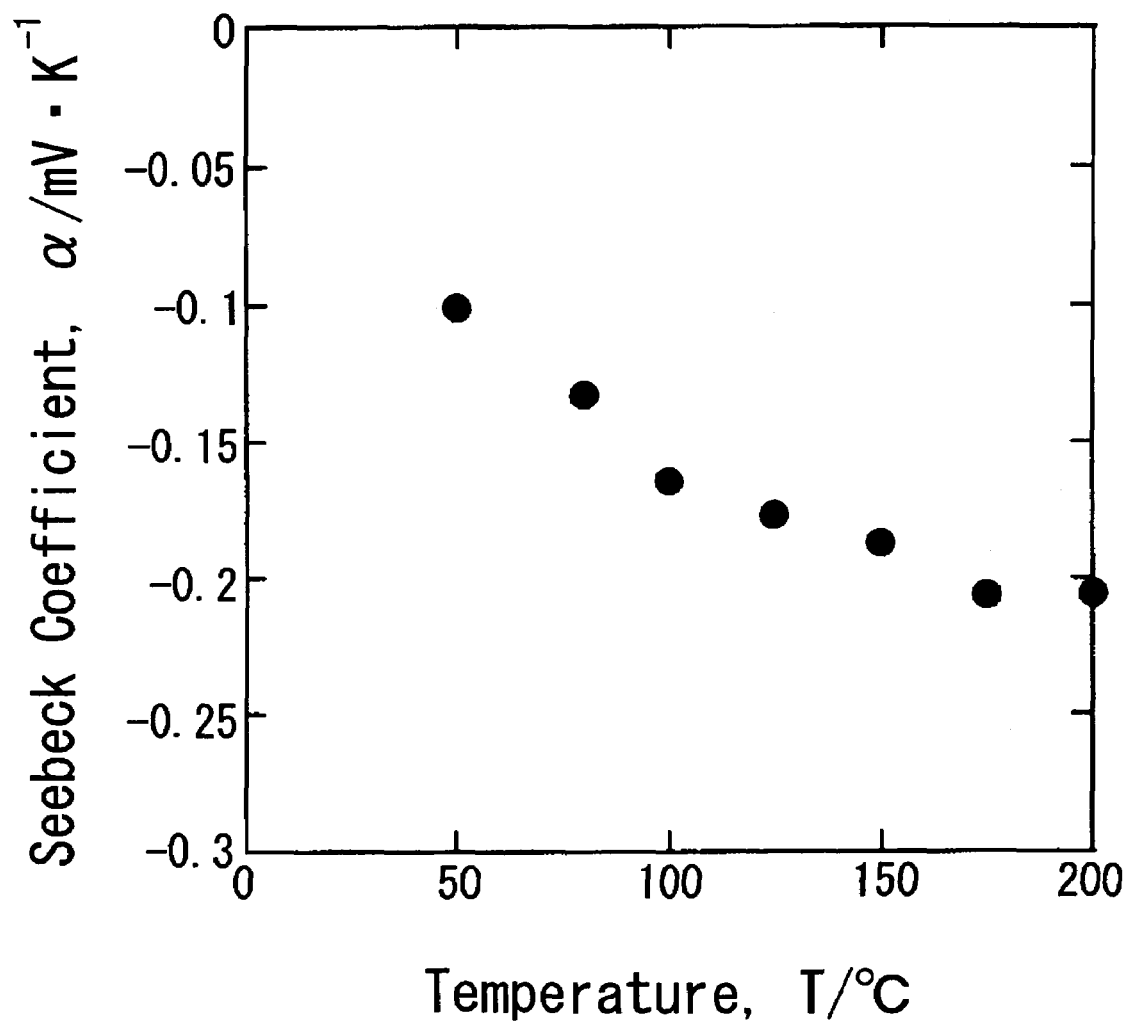
FIG. 8 is a graph of the temperature dependence of the Seebeck coefficient of an SiGe thin film.

When an SiGe target is pre-doped with an impurity, a problem is that the doped component (phosphorus) is evaporated by the heat treatment, which markedly reduces the doping amount, but if the vapor deposition conditions, such as the substrate temperature during sputtering vaporization, and the heat treatment conditions, such as the heat treatment temperature, are varied, then the doped component can be left intact. FIG. 8 shows the temperature dependence of the Seebeck coefficient of the sample in an example of this. The sample was produced by vapor deposition for 40 minutes at a sputtering output of 250 W and a substrate temperature of 200° C., using a phosphorus-doped SiGe target, performed for 5 hours at 800° C. while argon was allowed to flow through an ordinary electric furnace. As shown in FIG. 8, since the doped amount of phosphorus was sufficient, the Seebeck coefficient was negative over the entire temperature range, and n type characteristics were exhibited.

EXAMPLE 2

(1) Production of Gas Sensor

Figure 9:
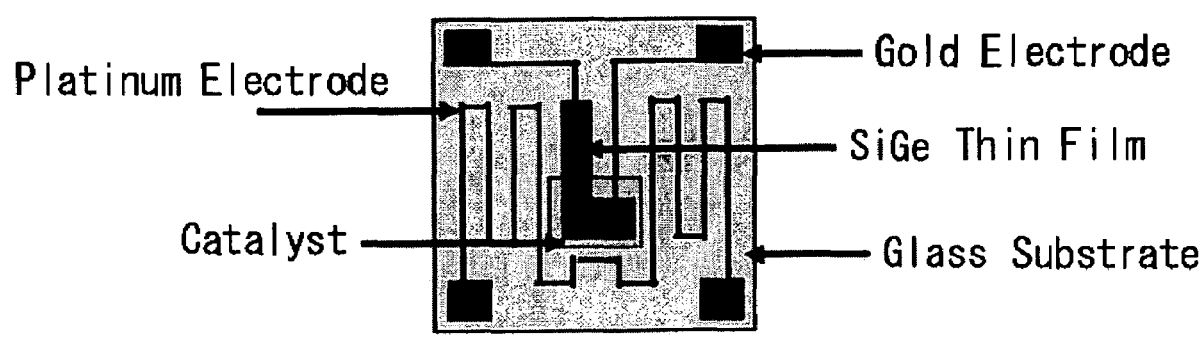
FIG. 9 shows a device pattern produced on a glass substrate.

In this example, the device was the same as the gas sensor in Example 1, but the design thereof was different, and in particular, a heater line was formed from platinum, and a mechanism for heating the device was formed simultaneously. The process was basically the same as that in Example 1, but differed in the following points. 1) A process in which nickel (a transition metal) was simultaneously sputtered was added in the sputtering vaporization of the SiGe. 2) Titanium (a transition metal) was formed as a buffer layer in order to increase adhesion to the substrate in the vapor deposition of the gold electrode pattern and the vapor deposition of the platinum heater. FIG. 9 shows the design of the device.

1) Thermoelectric Film Production

A film of a thermoelectric transducing material was formed under the same high frequency (RF) sputtering conditions as in Example 1, and a thin film of an SiGe thermoelectric transducing material was produced over glass. 7059 glass made by Corning was used as the substrate. Nickel was vapor deposited in a thickness of about 30 nanometers prior to the sputtering of the SiGe. The other conditions were basically the same as in Example 1.

2) Heat Treatment

The SiGe thin film produced by sputtering vaporization was placed in a furnace with an argon atmosphere and heat treated for about 6 hours between 500 and 600° C., which produced an SiGe thin film with increased crystallinity.

3) Heater Formation

After this, a heater line was formed by vapor depositing platinum over the above product. Titanium (a transition metal) was formed in a thickness of 50 nanometers as a buffer layer in order to increase adhesion to the substrate prior to the vapor deposition of platinum. The thickness of the platinum heater was approximately 1 micron. With the gold serving as an electrode, just as with the platinum, titanium (a transition metal) was formed in a thickness of 50 nanometers as a buffer layer.

(2) Results

The effects of the present invention will now be described on the basis of the results of evaluating the characteristics of the sensor device produced in the above process and its performance as a sensor.

1) Change in the Crystallization Temperature

Figure 10:
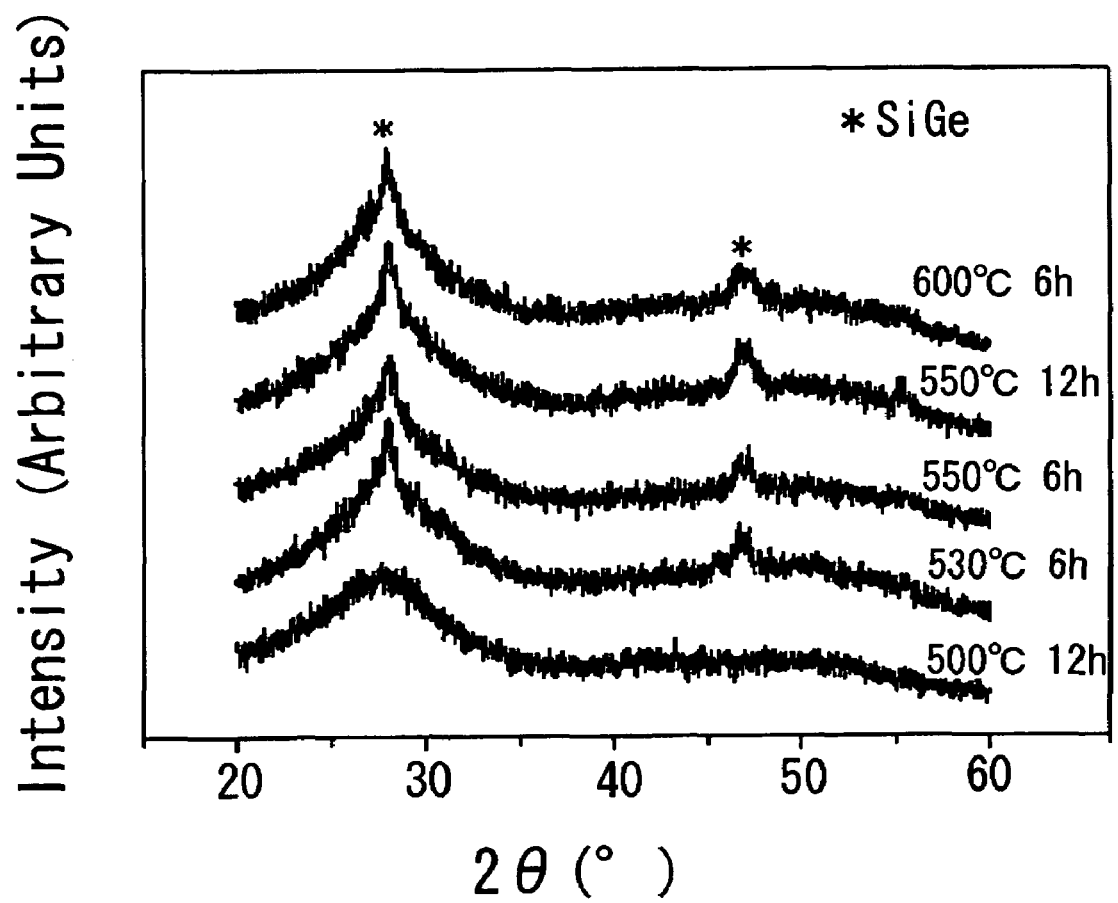
FIG. 10 shows the X-ray diffraction patterns of SiGe thin films as a function of heat treatment temperature after sputtering vapor deposition.

FIG. 10 shows the X-ray diffraction patterns of SiGe thin films as a function of heat treatment temperature after sputtering vaporization. It can be seen that when nickel was vapor deposited, the temperature of the heat treatment required for crystallization was several hundred degrees centigrade lower than in Example 1. This makes it clear that this is a particularly effective method for glass substrates that cannot be subjected to heat treatment at high temperatures.

2) Evaluation of Sensor Device

Figure 11:
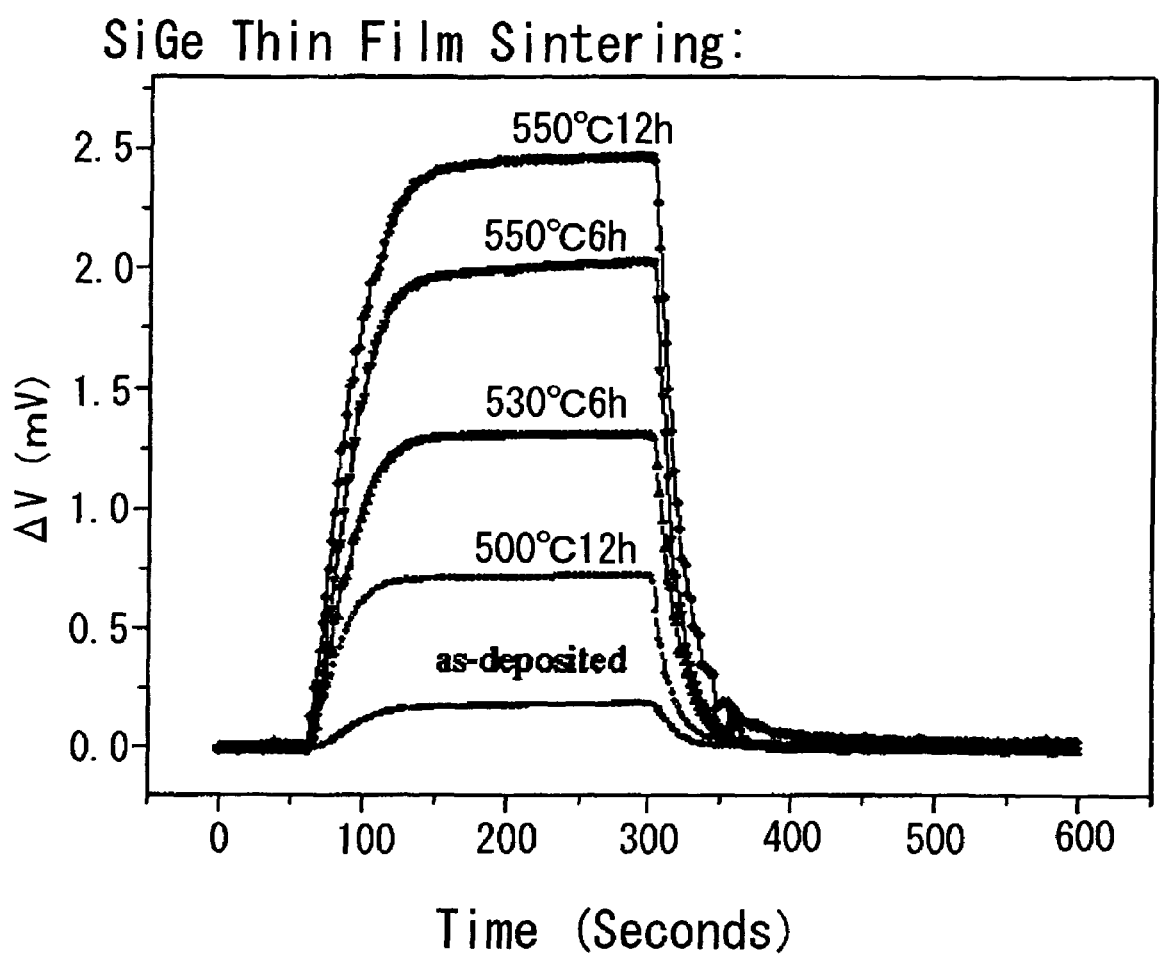
FIG. 11 shows the improvement in voltage signal and device characteristics as a function of heat treatment temperature.

A device produced using a glass substrate with the patterns shown in FIG. 9, produced using the same catalyst production process as in Example 1, was evaluated for response characteristics with respect to a hydrogen concentration of 3% at an operating temperature of 100° C. FIG. 11 shows the improvement in voltage signal and device characteristics as a function of heat treatment temperature. In Example 1, heat treatment at a high temperature of about 900° C. was necessary in order to reproduce adequate sensor response characteristics, but in this case adequately high sensor output was obtained even at a temperature as low as 550° C. Because a glass substrate was used, the heater power needed to maintain a sensor operating temperature of 100° C. was only about half that in Example 1.

EXAMPLE 3

This is an example of a manufacturing method that increases gas selectivity by forming a thin silicon oxide film on the surface of the gas sensor of Example 1.

(1) Production of Gas Selective Layer Formed on Catalyst Surface

1) Poisoning with HMDS

The gas selectivity of a sensor device can be increased by exposing a sensor device whose signal source converts a local temperature differential produced by a catalyst reaction into an electric signal to a volatile organosilicon gas to form a thin film on the surface thereof. The device temperature must be raised to a high temperature in order to form a film by chemical vapor deposition on a catalyst surface, but a problem with performing this process is that it adversely affects the properties of the catalyst. The thermoelectric gas sensor device used here was produced by the process of Example 1. After platinum catalyst vapor deposition, this device was placed in a sample treatment box with a 1000 ppm HMDS (volatile organosilicon) atmosphere, and the sample was poisoned for 3 days while the device operating temperature was held at 160° C. This poisoning process diminished the hydrogen response characteristics of the device by about half of their initial level.

2) Restorative Heat Treatment and Surface Analysis

The device was then subjected to heat treatment for 2 hours at 400° C. while argon was allowed to flow through an ordinary electric furnace. This restored the hydrogen response characteristics. Since a tough silicon oxide layer is produced over the platinum surface if the device temperature is high, there was no further restoration of response characteristics after subsequent heat treatment. XPS analysis results revealed that silicon oxide is what was formed on the surface. In particular, it was found that with a sample pronounced restoration characteristics, the O1s and Si2p contents were lower than before poisoning, and a layer having chemical bonds of oxygen and silicon on the platinum surface was removed by heat treatment.

(2) Evaluation of Sensor Device

With a poisoned sample having an extremely thin silicon oxide film, this film had the effect of suppressing reactions with gases other than hydrogen, and even when the operating temperature was as high as 160° C., the S value for hydrogen selectivity, particularly with respect to large gas molecules such as ethanol or methanol, was higher than with an unpoisoned sample having no silicon oxide film. The curve of response characteristics was basically the same as that in Example 1 or 2. However, the signal output varied further with the type of gas before the poisoning treatment and following the restoration treatment performed after poisoning treatment.

Table 1 lists the voltage output of the sensor with respect to a hydrogen concentration of 3% at a device operating temperature of 160° C. The selectivity S is the relative size of the signal when the output with respect to hydrogen gas is set at 1. Accordingly, hydrogen has an S value of 1, and this is not shown in Table 1. First, with a device that underwent everything up to the restoration treatment, the voltage signal decreased to 87% of what it had been prior to poisoning. However, hydrogen selectivity was improved by this treatment. When the device operating temperature was high, flammable gases such as methanol or ethanol were prone to catalytic combustion, and became a problem as interfering gas, but because of this molecular sieve-like surface layer, these reactions were suppressed, and sensor output for these larger molecules decreased. For example, the output was 6.5 times less in the case of methanol, and was 6.2 times less in the case of ethanol. Because there was little decrease for hydrogen, the hydrogen selectivity S improved markedly.

treatment duration shortened by changing the process conditions in sputtering vaporization and performing rapid heating. The electroconductivity of a thermoelectric transducing thin film material can be controlled by controlling the heat treatment conditions. An oxide thin film produced during heat treatment can be utilized as the insulation layer required for device production. The temperature of heat treatment required for SiGe crystallization can be lowered by introducing nickel during sputtering vaporization, allowing a thin film to be formed on a substrate that is not stable at high temperatures, such as glass or plastic. Also, hydrogen gas selectivity can be increased by forming a thin layer like a molecular sieve from volatile organosilicon on a catalyst surface, and controlling the film production conditions and so forth.

The invention claimed is:

1. A method for producing an SiGe-based semiconductor thin film to be served as a member of a thermoelectric transducing material component that is a constituent element of a sensor device whose signal source is a temperature differential and that transduces a local temperature differential produced by a selective catalyst reaction into an electric signal, comprising the steps of:
   (1) forming an SiGe-based semiconductor thin film over a substrate by sputtering vaporization; and
   (2) heat treating the SiGe-based semiconductor thin film material after the sputtering vaporization.

2. The method according to claim 1, wherein the heat treatment is performed at a temperature of from 600° C. to 1000° C.

3. The method according to claim 1, wherein the substrate temperature and/or the plasma output is raised in the formation of a SiGe-based semiconductor thin film by sputtering vaporization method, to form a thin film with a more highly crystallized structure.

4. The method according to claim 1, wherein the heat treatment is performed by furnace annealing with a controlled atmosphere using an ordinary electric furnace, or by rapid thermal process using an infrared lamp heating apparatus capable of atmosphere control.

TABLE 1

| Conditions | $H_2$ | CO | | $CH_4$ | | $i\text{-}C_4H_{10}$ | | $C_2H_5OH$ | | $CH_3OH$ | |
|---|---|---|---|---|---|---|---|---|---|---|---|
| Poisoning | Vs | Vs | S | Vs | S | Vs | S | Vs | S | Vs | S |
| Before | 7.871 | 0.076 | 104 | 0.126 | 63 | 0.282 | 28 | 0.459 | 17 | 0.673 | 11 |
| After | 6.865 | 0.059 | 116 | 0.108 | 64 | 0.106 | 65 | 0.074 | 93 | 0.103 | 67 |

INDUSTRIAL APPLICABILITY

As discussed in detail above, the present invention relates to an SiGe-based thin film, to a method for manufacturing this film, and to a sensor device. With the present invention, it is possible to produce, by sputtering, an SiGe-based semiconductor thin film that has excellent thermoelectric performance as a member of a thermoelectric transducing material component that is a constituent element of a sensor device whose signal source is a temperature differential and that transduces a local temperature differential into an electric signal. Also, crystallinity can be increased and the required characteristics imparted by heat treating the thin film material after SiGe vapor deposition. Further, the temperature of the heat treatment can be lowered and the 5. The method according to claim 1, wherein, during sputtering, a thin film is produced by first doping an SiGe target with an impurity, and during heat treatment, the gas atmosphere, temperature, heat treatment duration, and temperature elevation time are controlled, so that crystallization is performed while the amount of impurity in the semiconductor thin film is controlled.

6. The method according to claim 1, wherein, during heat treatment, the heat treatment conditions are controlled, an insulator thin film of an oxide is grown over the semiconductor thin film, and crystallization is performed while an insulation layer is produced.

7. The method according to claim 1, wherein, during the sputtering vaporization of the SiGe-based thin film, the temperature of the heat treatment can be lowered by vapor depositing a transition metal typified by nickel.

8. The method according to claim 1, wherein a sensor device whose signal source transduces a local temperature differential produced by a selective catalyst reaction into an electric signal is exposed to a volatile organosilicon gas to form a thin film on the surface thereof, thereby increasing the gas selectivity thereof.

9. An SiGe-based thin film produced by the method according to any of claims 1 to 8, which serves as a member of a thermoelectric transducing material component that is a constituent element of a sensor device whose signal source is a temperature differential and that transduces a local temperature differential into an electric signal, and which has been endowed with good thermoelectric characteristics by heat treatment.

10. A gas sensor device containing as a constituent element the SiGe-based thin film according to claim 9.

* * * * *